(12) United States Patent
Choi et al.

(10) Patent No.: US 8,652,185 B2
(45) Date of Patent: Feb. 18, 2014

(54) APPARATUS FOR STIMULATING THE BRAIN AND MEASURING THE LIGHT INDUCED NEURONAL ACTIVITY AND METHOD FOR MANUFACTURING THE SAME

(75) Inventors: Ji Hyun Choi, Seongnam-si (KR); Guk Bae Kim, Pohang-si (KR); Hee Sup Shin, Eiwang-si (KR)

(73) Assignee: Korea Institute of Science and Technology, Seoul (KR)

( * ) Notice: Subject to any disclaimer, the term of this patent is extended or adjusted under 35 U.S.C. 154(b) by 782 days.

(21) Appl. No.: 12/551,599

(22) Filed: Sep. 1, 2009

(65) Prior Publication Data

US 2010/0161017 A1 Jun. 24, 2010

(30) Foreign Application Priority Data

Dec. 23, 2008 (KR) ........................ 10-2008-0132365

(51) Int. Cl.
*A61N 5/06* (2006.01)
(52) U.S. Cl.
USPC .......................................................... 607/88
(58) Field of Classification Search
USPC ................ 607/88, 92, 96; 600/544, 476, 321
See application file for complete search history.

(56) References Cited

U.S. PATENT DOCUMENTS 6,600,943 B1 * 7/2003 Kiuchi et al. ................. 600/407
7,010,356 B2 * 3/2006 Jog et al. ....................... 607/116
7,133,714 B2 * 11/2006 Karmarkar et al. ........... 600/423

FOREIGN PATENT DOCUMENTS

JP 2000-262460 9/2000
KR 10-0383476 B1 7/1997
KR 1020080100573 A 11/2008

OTHER PUBLICATIONS

Notice of Allowance dated Jul. 8, 2011 corresponding to the Korean Patent Application No. 10-2008-0132365.

* cited by examiner

*Primary Examiner* — Jessica Stultz
*Assistant Examiner* — Tuan Nguyen
(74) *Attorney, Agent, or Firm* — Ohlandt Greeley Ruggiero & Perle L.L.P.

(57) ABSTRACT

Disclosed is an apparatus for stimulating the brain and measuring the light induced neuronal activity including a signal application unit which applies a signal to a living tissue to stimulate the neuronal cells in the living tissue; an electrode unit which detects an electrophysiological signal of the neuronal cell in response to the signal; and an insulation unit which controls an impedance of the electrode unit. The signal application unit is formed integrally with the electrode unit, so that the site where the signal is applied to the living tissue is approximated to the site where the response to the stimulation is measured.

12 Claims, 6 Drawing Sheets

APPARATUS FOR STIMULATING THE BRAIN AND MEASURING THE LIGHT INDUCED NEURONAL ACTIVITY AND METHOD FOR MANUFACTURING THE SAME

CROSS-REFERENCE TO RELATED APPLICATIONS

This application claims priority to Korean Patent Application No. 10-2008-0132365, filed on Dec. 23, 2008, and claims all the benefits accruing therefrom under 35 U.S.C. §119. Korean Patent Application No. 10-2008-0132365 is herein incorporated by reference in its entirety.

BACKGROUND

1. Field

This disclosure relates to an apparatus for stimulating the brain and measuring the light induced neuronal activity capable of stimulating the brain during an experiment on a living body and of minimizing damage to the brain during insertion of the apparatus. Further, this disclosure relates to an apparatus capable of improving measuring efficiency by approximating the site where the stimulation is applied to the site where the measurement is made.

2. Description of the Related Art

Neuropsychiatric diseases are known to develop in the neural circuit level starting from the abnormality of specific neural cells (neurons). For example, Parkinson's disease is known to result from the loss of dopaminergic neurons in the substantia nigra. For the treatment of neuropsychiatric diseases, operations such as deep brain stimulation (DBS), transcranial magnetic stimulation (TMS), vagus nerve stimulation (VNS), etc. are performed in addition to medication. These methods are disadvantageous in that it is difficult to treat the diseases elaborately and systematically in the signaling level of the neural circuit.

Recently, in the field of brain research, light-sensitive proteins have been developed, which react in response to light of specific wavelength to activate or inhibit neurons. Using them, it is possible to control the neurons in the neural circuit more freely and elaborately. The past electrical-type micro-stimulants had several limitations as follows. First, due to the heterogeneity of brain tissue, it is unclear which circuit elements are responsible for the therapeutic effects. Second, the electrical-type micro-stimulant is intrinsically a complicated manipulation because target neurons can respond with increased, decreased, or mixed temporal patterns of activity; as a result the magnitude and even the sign of target cell responses to the electrical stimulants are unknown. Finally, it is difficult to assess the net outcome of the electrical-type micro-stimulants on overall activity in the target cells and region, because electrical stimulation creates artifacts that prevent direct observation of local circuit responses during the electrical stimulation itself.

In contrast, optical stimulation of neurons is advantageous in that the target neurons can be freely selected by using different promoters. In addition, once the light-sensitive protein is expressed in the target neurons, activation and inhibition thereof can be controlled freely by controlling the wavelength range of the optical stimulation. Therefore, the optical stimulation allows more elaborate and systematic study of the neural circuit. Further, it helps to understand what specific brain neurons are related with a particular neuropsychiatric disease and how a problem occurs in the neural circuit.

In technical sense, to realize the optical stimulation of neurons in a living body (in vivo), it is very important to insert an optic fiber in the brain more stably. Further, in many cases, a recording electrode is inserted together in order to verify whether the light-sensitive protein was sufficiently expressed in the target area of the neurons. In experiments using small animals such as mouse, there is a high risk of damage to the brain during the insertion of this electrode-coupled optic fiber. Moreover, in the actually inserted optic fiber and a electrode couple, the site at which optical stimulation is applied by the light emitted from the optic fiber is not identical to the site of measurement (distant by about 0.125 mm (millimeter) or more). As a result, the measuring efficiency of the activation and inhibition of neurons by the optical nerve stimulation is very low.

Accordingly, there is a need of an apparatus for stimulation and detection capable of performing optical stimulation of neurons stably and efficiently, and a method for manufacturing the same.

BRIEF SUMMARY OF THE INVENTION

In order to solve the problems of the existing art, there are provided an apparatus for stimulating the brain and measuring the extracellular activity of neurons by stimulation, wherein the part being inserted in a living body is tapered, the site where the stimulation is applied is approximated to the site where the measurement is made, and an area of the effective area of a signal stimulating a tissue may be controlled, and a method for manufacturing the same.

The apparatus for stimulating the brain and measuring the light-induced neural activities includes a light application unit which applies a light to a living tissue to activate or inhibit the living neuronal cells; an electrode unit which detects an electrical signal of the living tissue in response to the signal; and an insulation unit which controls the impedance of the electrode unit, wherein the light application unit is formed integrally with the electrode unit.

And, the method for manufacturing the apparatus for stimulating the brain and measuring the light-induced neuronal activity includes coupling a plurality of the light signal application units; tapering an end of the signal application unit; coating an electrode unit on the surface of the signal application unit; and coating an insulation unit on the surface of the electrode unit. By controlling the area of the insulation unit coated on the surface of the electrode unit, it is possible to control the impedance of the electrode unit.

The apparatus according to this disclosure may reduce the insertion volume directly damaging brain tissue and neurons by up to 70% as compared with the existing art. And, as the end of the signal application unit or optic fiber inserted in the tissue is tapered, the phenomenon of the tissue being pushed during the insertion is reduced and, thus, and the sequelae following the insertion is minimized.

The efficiency of the disclosed system may be maximized by approximating the site where an optical stimulation is generated by the signal application unit or optic fiber to the site where a response to the stimulation is recorded by the electrode unit within a predetermined distance. Further, the impedance value of the electrode may be controlled freely by adjusting the coating area of insulator.

In addition, in case blue light and yellow light are applied simultaneously, the target neurons in a small area of a living body may be accurately activated since the irradiation area of the yellow light can be controlled freely.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Figure 1:
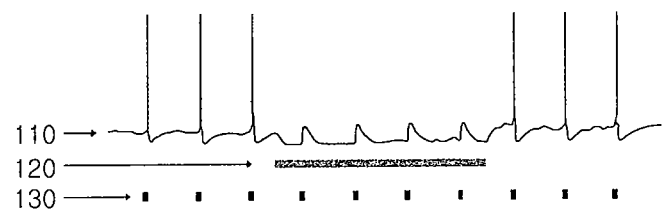
FIG. 1 shows the neural response when blue light for tissue activation and yellow light for tissue inhibition are applied simultaneously.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

An optic fiber and a recording electrode couple used in a general optical nerve stimulation system are obtained simply by attaching an optic fiber to an electrode.

Because of a relatively large volume, the apparatus inevitably damages the brain when inserted in the brain. In accordance with this disclosure, such damage may be reduced by tapering an end of a signal application unit or optic fiber inserted in a tissue.

The area where the light actually arrives is small, with a diameter of several micrometers (μm(micrometer)). Therefore, there is no problem in light transmission even when an end of the signal application unit or the optic fiber is tapered.

In general, optical nerve stimulation is performed by using blue light (wavelength: 470 nm (nanometer)) and yellow light (wavelength: 580 nm (nanometer)) simultaneously. The blue light activates neurons, while the yellow light inhibits them.

FIG. 1 shows the neural response when blue light for neuronal activation and yellow light for neuronal inhibition are applied simultaneously. As seen in FIG. 1, when an optical response activating light-sensitive cation channel of ChR2 which activates neurons in response to blue light and an optical response activating light-sensitive anion pump of NpHR which inhibits the neurons in response to yellow light are expressed simultaneously, and if the yellow light 120 and blue light 130 are applied simultaneously to the neurons, so that the result of the neural response 110 is that the inhibition response inhibits the activation response.

Figure 2:
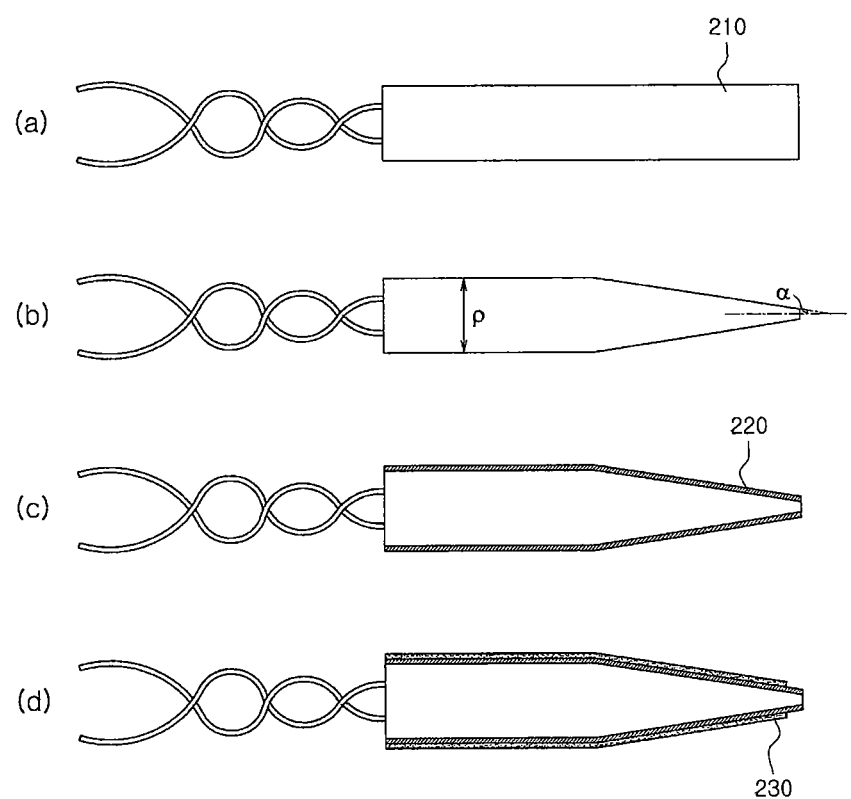
FIG. 2 shows a process of manufacturing an apparatus for stimulating the brain and measuring the light-induced neural activity signals according to this disclosure.

FIG. 2 shows a process of manufacturing an apparatus for stimulating the brain and measuring the light induced neuronal activity according to this disclosure.

First, a signal application unit is formed in FIG. 2(a). In an embodiment, two optic fibers are joined together, so that two lights may be injected in the optic fibers, respectively, and applied through end of the one optic fiber. In accordance with this disclosure, instead of the optic fiber in the existing art, two optic fibers which transmit two lights are joined into one piece. In an embodiment of joining into one piece, two optic fibers may be joined by twisting and joining the ends of optic fibers with tension of heat. The joined optic fiber 210 constitutes a signal application unit. The signal application unit applies a signal to a living tissue to stimulate the neurons.

The application unit may be formed by various methods, an example of which will be described referring to FIG. 5.

Next, an end of the signal application unit or optic fiber inserted in a living tissue is tapered in FIG. 2(b). This is in order to minimize damage to the living tissue during the insertion and after implantation following the insertion. The angle alfa (α) or diameter rho (ρ) of the tapering may be determined through experiments. Specifically, the angle alfa (α) of the tapering may be determined by transmission efficiency, process, application or target resolution, etc. The angle of the tapering may range from 10 degrees to 60 degrees to minimize damage to the living tissue during the insertion. According to the pull methods, an optical fiber is heated with laser, so that the optical fiber may become soft. Then, the optical fiber is pulled with a puller mechanically and cut to have a thin end. As a result of the process of pulling, the angle of the optical fiber may range from 20 degrees to 80 degrees. Or the optical fiber can be tapered by etching method by inserting the end of the optical fiber in etchant. The angle of the optical fiber may be controlled from 5 degrees to 30 degrees by controlling the etching duration. The diameter rho (ρ) of the apparatus may range from 50 micrometers (μm) to 200 micrometers (μm).

Next, unlike the existing method of attaching a recording electrode, a metallic material 220 is directly plated, doped or coated on the signal application unit or optic fiber in FIG.

2(c). In the existing art, a recording electrode which is prepared specially is simply attached to an optic fiber by glue. In contrast, in accordance with this disclosure, the surface of the signal application unit or optic fiber is enclosed by an electrode. In this way, the optic fiber is formed integrally with the recording electrode.

In the existing art, the site where a stimulation signal is applied is distant from the site where a response to the signal is recorded. Since this distance is about 0.125 mm (millimeter) or larger, the efficiency of measuring the activation or inhibition signal decreases. In accordance with this disclosure, this problem can be improved because the site where a signal is applied may be approximated to the site where a recording is made.

At last, after enclosing the surface of the optic fiber with the metallic material, the metallic material is coated with an insulating material 230 except for a contact portion for the measurement in FIG. 2(d). By controlling the area of the contact portion for the measurement, the site where the recording is made may be controlled to have various impedance values.

Figure 3:
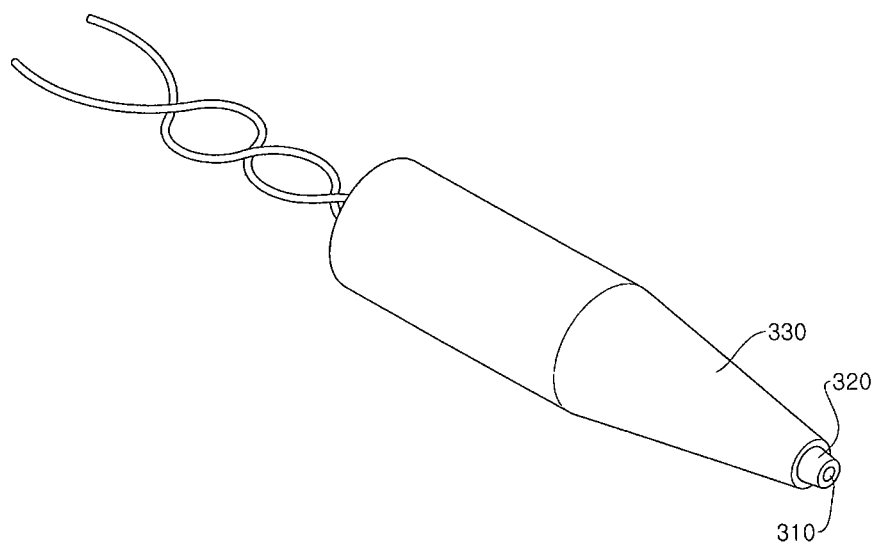
FIG. 3 shows a schematic perspective view of an apparatus for stimulating the brain and measuring the stimulated neural activity.

FIG. 3 shows a schematic perspective view of an apparatus for stimulating the brain and measuring the light induced neuronal activity. The apparatus for stimulating the brain and measuring the light induced neuronal activity according to this disclosure comprises a signal application unit 310 which applies a signal of light to a living tissue; an electrode unit 320 which detects a reaction of the neurons in response to the light signal; and an insulation unit 330 which controls an impedance of the electrode unit. By forming the signal application unit integrally with the electrode unit, the site where the living tissue is stimulated by the signal may be approximated to the site where the response to the stimulation is measured. Further, the stimulation of the neuronal cells by the light signal and the measurement of the light induced neuronal activity to the stimulation may be carried out simultaneously.

In the apparatus according to this disclosure, the site where the stimulating is applied and the site where the recording is made are not separated, but they are approximated as in FIG. 3.

An end of the signal application unit is tapered. This is in order to minimize the damage to the living tissue during insertion of the apparatus and the sequelae following the insertion. If the site where the signal is applied and the site where the recording is made are separated from each other, the area or volume for insertion in the living tissue is about two times that of this disclosure.

Figure 4:
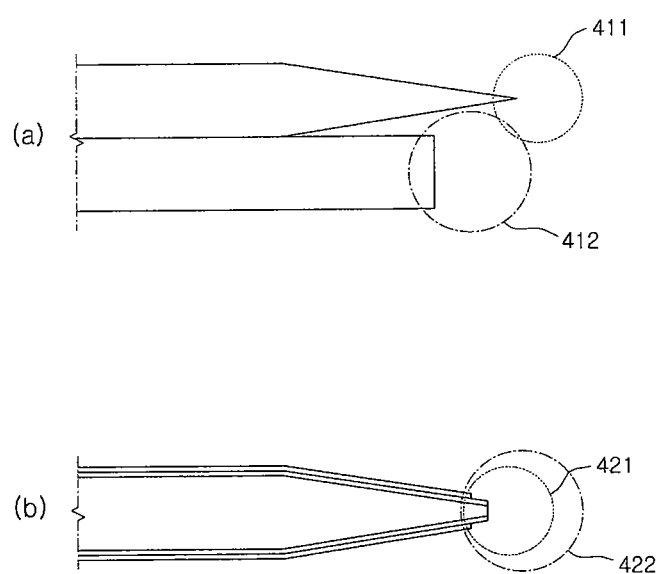
FIG. 4 compares apparatuses for stimulating the brain and measuring the stimulated neural activity according to the existing art and according to this disclosure.

FIG. 4 compares apparatuses for an optic fiber and a recoding electrode couple according to the existing art and stimulating the brain and measuring the neuronal activity according to this disclosure. FIG. 4(a) shows an optic fiber and a recording electrode according to the existing art. FIG. 4(b) shows an apparatus for stimulating the brain and measuring the neuronal activity according to this disclosure. Referring to FIG. 4(a), the site where a recording is made 411 is distant from the site where a light signal is applied 412. In contrast, referring to FIG. 4(b), the site where a recording (or detection) is made 421 is approximated to the site where a light signal is applied 422. In addition, the two apparatuses have different volumes.

Referring again to FIG. 3, the signal application unit is located at the innermost core and the electrode unit is located on the signal application, and the insulation unit is located on the electrode unit. That is, the electrode unit encloses the signal application unit, and the insulation unit encloses the electrode unit. The insulation unit does not entirely enclose the electrode unit, but remain the portion for the recording or detection of the tissue response. The way of laminating the electrode unit and the insulation unit are laminated on the signal application unit as follows. The electrode unit is laminated on the signal application unit by plating, doping or coating. The insulation unit is laminated on the electrode unit by coating.

The signal application unit may comprise a plurality of optic fibers. Referring to FIG. 3, the signal application unit comprises two strands. The two strands may be two of optic fibers. The reason why a plurality of optic fibers is used to constitute the signal application unit is to enable simultaneously to apply a signal that activates neuronal cells and a signal that inhibits the neuronal cells.

The way of joining the plurality of optic fibers at one end as illustrated in FIG. 3, illustrated in FIG. 2. FIG. 2 shows an example of using two optic fibers. The optic fibers are twisted and heated, so that the optic fibers are joined into one piece at end thereof. The joined end is tapered and used for the apparatus according to this disclosure.

The signal applied by the signal application unit may include an activation signal and an inhibition signal. The activation signal is a signal of a wavelength region that activates neuronal cells, and the inhibition signal is a signal of a wavelength region that inhibits the neuronal cells. The apparatus according to this disclosure may activate and inhibit the neuronal cells simultaneously, by applying the two signals to a neuronal cell. A further description about the signal will be given later referring to FIG. 5.

In another embodiment, the signal application unit of the apparatus according to this disclosure may comprise a plurality of signal passages each comprising a signal transmitter which transmits and irradiates the signal and a clad which encloses the signal transmitter.

Among the plurality of signal passages, the innermost signal passage is formed as a core shape, and the remaining plurality of signal passages are laminated around the innermost signal passage. For example, the innermost signal passage may have a cylindrical shape, as illustrated in FIG. 5. As signal passages are laminated around the cylindrical innermost signal passage, the resultant signal application unit has a cylindrical shape.

The clad allows each of the signal transmitters to transmit and irradiate a signal of a wavelength region. Through this configuration, it is possible to control the effective area of the activation signal transmitted and irradiated by the signal transmitter.

If the refractive index of the clad is made smaller than the refractive index of the signal transmitter enclosed by the clad, the signal transmitted to the signal transmitter is totally reflected at the boundary with the clad. Therefore, a signal of one wavelength region may be transmitted and irradiated in one signal transmitter. Accordingly, if a plurality of signal transmitters and a plurality of clads are laminated alternately, a plurality of signals may be transmitted and irradiated through the signal application unit.

When stimulating a tissue and measuring a neuronal response to the stimulation using an optic fiber and a recording electrode couple according to the existing art, there is a problem that the area for activating or inhibiting the tissue cannot be controlled. Using the apparatus according to this disclosure, the way is suggested to control the area for activating or inhibiting the tissue may be controlled as follows.

In order to control the area for activating or inhibiting the tissue, the region where the activation signal is irradiated is overlapped with the region where the inhibition signal irradiated. If the two regions are overlapped, the two signals are offset and the region where the activation signal is not offset by the inhibition signal remains depending on the configuration of the signal application unit. By controlling the area of this region, an adequate amount of light required to stimulate the tissue may be ensured.

In order to make the two regions to overlap with each other, one or more of the distance between each signal transmitter, the cross section of the signal transmitter by which the inhibition signal is transmitted, and the intensity of the inhibition signal may be controlled. Depending on the configuration of the signal application unit, the range of the signal irradiated by each signal transmitter is different. By controlling one or more of the distance between each signal transmitter, the cross section of the signal transmitter by which the inhibition signal is transmitted, and the intensity of the inhibition signal, the area of the activation signal required for the stimulation may be attained.

Figure 5:
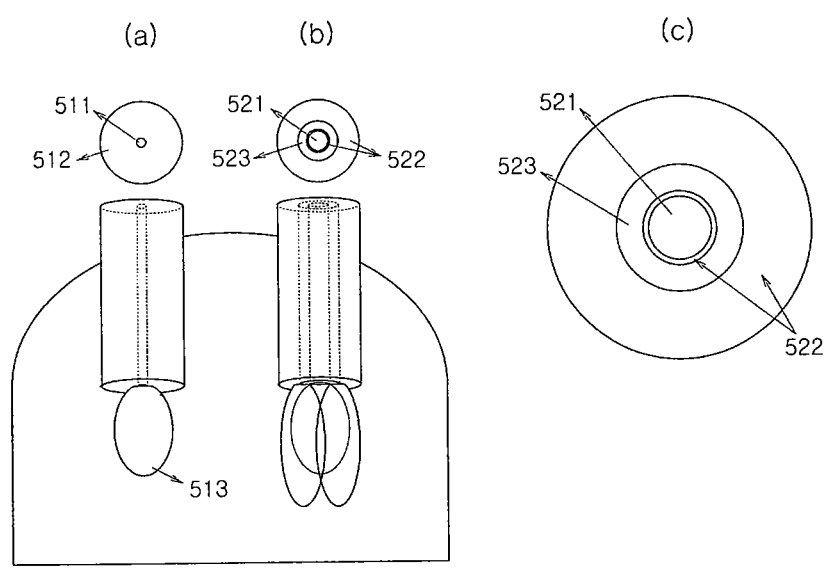
FIG. 5 shows the configuration of a signal application unit of an apparatus for stimulating the brain and measuring the stimulated neural activity according to this disclosure.

FIG. 5 shows a signal application unit of an apparatus for stimulating the brain and measuring the light induced neuronal activity according to another embodiment. In this another embodiment, a signal application unit comprising a signal transmitter and a clad has a cylindrical shape. In FIG. 5, the signal application unit is configured using two signal transmitters and two clads. FIG. 5(a) shows an existing general optic fiber, FIG. 5(b) shows a signal application unit according to this disclosure, and FIG. 5(c) shows the cross section of FIG. 5(b).

The signal application unit according to this embodiment may comprise a first signal transmitter which transmits an activation signal; a second signal transmitter which transmits an inhibition signal; a first clad; and a second clad. The first clad encloses the first signal transmitter, the second signal transmitter encloses the first clad, and the second clad encloses the second signal transmitter. By controlling the effective area of the region where the activation signal is irradiated by the first signal transmitter, a stimulation required to activate a neuronal cell may be provided.

Among the way of controlling the effective area of the signal, by controlling one or more of the distance between the first signal transmitter and the second signal transmitter, the cross section of the second signal transmitter, and the intensity of the signal transmitted by the second signal transmitter, the effective area of the activation signal transmitted by the first signal transmitter may be controlled. More specifically, the effective area of the activation signal may be controlled by offsetting the activation signal with the inhibition signal. The method of controlling the effective area of the signal will be described in more detail.

As seen in FIG. 5(a), an optic fiber generally consists of a core 511 for transmitting light, and a clad 512 having a relatively low refractive index to totally reflect the light transmitted to the core. The light irradiated by an optic fiber is emitted at the end of the optic fiber. As seen in FIGS. 5(a) and (b), if an end of the optic fiber or signal application unit is inserted in a medium like a living tissue, the range of the light which is effectively transmitted as an optical stimulation, the range of activating the neurons, corresponds to a region 513 of FIG. 5(b).

It is known that a minimal intensity of irradiation for optical stimulation in vivo is about 380 mW/mm$^2$ (milliwatt per square millimeter). The problem is that, if the output of the light source is increased to ensure the final transmission intensity of light, the range of the region 513 cannot be controlled. That is to say, it is impossible to confine an effective light transmission area within range of region 513 while ensuring the minimal intensity of light required for the neuronal activation.

In order to solve this problem, two signal passages are configured to transmit blue light and yellow light simultaneously, as illustrated in FIGS. 5(b) and (c). Each of the signal passages consists of a signal transmitter and a clad. In FIG. 5(c), if the refractive indices $n_a$ (n sub-a) and $n_c$ (n sub-c) of the signal transmitters 521, 523, respectively, are larger than the refractive index $n_b$ (n sub-b) of the clad 522, light may be transmitted by the two signal transmitters 521, 523, respectively. If the signal transmitters 521, 523 are made with suitable materials, although two light are transmitted simultaneously, the signal transmitter 521 may be transmitted blue light only, and the signal transmitter 523 may be transmitted yellow light only.

By controlling the distance between the signal transmitters 521, 523, the cross section of the signal transmitter 523, and the intensity of the yellow light transmitted by the signal transmitter 523, it is possible to precisely control the effective area of the blue light for activating neurons transmitted by the signal transmitter 521.

Figure 6:
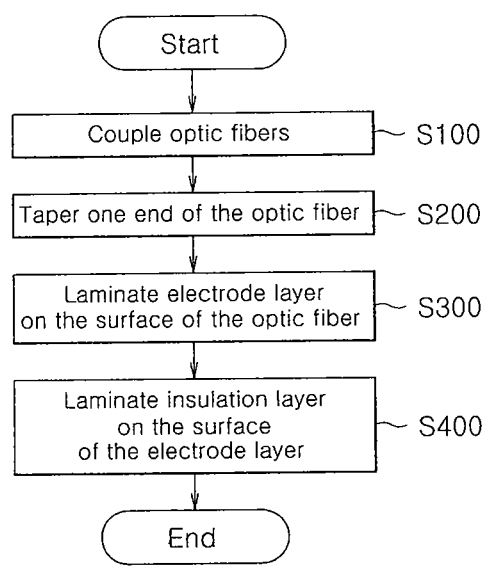
FIG. 6 is a flow chart illustrating a method for manufacturing an apparatus for stimulating the brain and measuring the stimulated neural activity according to this disclosure.

FIG. 6 is a flow chart illustrating a method for manufacturing an apparatus for stimulating the brain and measuring the light induced neuronal activity according to this disclosure. The method for manufacturing the apparatus according to this disclosure is also described referring to FIG. 2. The method for manufacturing the apparatus according to this disclosure comprises coupling a plurality of signal application units (S100); tapering an end of the signal application unit (S200); laminating an electrode unit on the surface of the signal application unit (S300); and laminating an insulation unit on the surface of the electrode unit (S400). The impedance of the electrode unit may be controlled by controlling the area of the insulation unit laminated on the surface of the electrode unit.

As the electrode unit and the insulation unit are laminated, the electrode unit encloses the signal application unit and the insulation unit encloses part of the surface of the electrode unit. When the insulation unit encloses the electrode unit, part of the electrode unit is remained without being enclosed, so that an end portion of the electrode unit may be in contact with the living tissue. The electrode unit encloses the signal application unit by plating, doping or coating, and the insulation unit encloses the electrode unit by coating.

In an embodiment of coupling the plurality of signal application units, a plurality of optic fibers may be twisted and heated to join the ends of the optic fibers into one piece.

In another embodiment of the method for manufacturing the apparatus according to this disclosure, the apparatus may be configured so that the area of the region where the signal is applied by the signal application unit may be controlled. The signal application unit may comprise a plurality of signal passages each comprising a signal transmitter which transmits and irradiates a signal and a clad which encloses the signal transmitter. The signal may include one or more of a signal activating a neuronal cell and a signal inhibiting the neuronal cell.

Said coupling of the signal application units (S100) may comprise laminating a clad on a signal transmitter; and laminating a signal transmitter on the clad which laminates the signal transmitter. By repeatedly laminating the signal transmitter and the clad, a smaller effective area of signal may be attained as compared when the signal is applied using a single optic fiber system.

In another embodiment of the method for manufacturing the apparatus according to this disclosure, the signal application unit may comprise a first signal transmitter which transmits an activation signal; a second signal transmitter which transmits an inhibition signal; a first clad; and a second clad. In this case, said coupling of the signal application unit may comprise laminating the first clad on the first signal transmitter; laminating the second signal transmitter on the first clad;

and laminating the second clad on the second signal transmitter and then, the signal application is coupled.

The refractive index of the first clad may be made smaller than the refractive index of the first signal transmitter, and the refractive index of the second clad may be made smaller than the refractive index of the second signal transmitter, so that each signal transmitter can transmit a signal of one wavelength region.

Further, the area of the region at which the signal is stimulated by the apparatus may be controlled. In the procedure of manufacturing the apparatus, the effective area of the activation signal transmitted by the first signal transmitter may be controlled by controlling one or more of the distance between the first signal transmitter and the second signal transmitter, and the cross section of the second signal transmitter.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. An apparatus for stimulating the brain and measuring the light induced neuronal activity comprising:
    a signal application unit which applies a signal to a living tissue to stimulate the living tissue including neuronal cells;
    an electrode unit which detects an electrophysiological signal of the living tissue in response to the signal; and
    an insulation unit which controls an impedance of the electrode unit,
    wherein the signal application unit is formed integrally with the electrode unit,
    wherein the electrode unit encloses the signal application unit and the insulation unit encloses part of the electrode unit,
    wherein the area of the electrode unit enclosed by the insulation unit controls a contact area of the electrode unit with the living tissue thereby controlling an impedance value of the electrode unit,
    wherein the signal application unit comprises a plurality of optic fibers, wherein the plurality of optic fibers are twisted and heated to join the ends of optic fibers into one piece,
    wherein the signal applied to the living tissue by the signal application unit includes an activation signal and an inhibition signal, and the neuronal cells in living tissue may be activated or inhibited,
    wherein the signal application unit comprises a first signal transmitter which transmits the activation signal, a second signal transmitter which transmits the inhibition signal, a first clad, and a second clad,
    wherein the first clad encloses the first signal transmitter, the second signal transmitter encloses the first clad, the second clad encloses the second signal transmitter, so that an effective treatment area of activation or inhibition is controlled, and
    wherein the second signal transmitter has a cylindrical shape having a hollow inner space, and wherein the first signal transmitter and the first clad are disposed in the hollow inner space of the second signal transmitter.

2. The apparatus for stimulating the brain and measuring the light induced neuronal activity according to claim 1, wherein an end of the signal application unit is tapered.

3. The apparatus for stimulating the brain and measuring the light induced neuronal activity according to claim 1, wherein the electrode unit is formed to enclose the signal application unit by plating, doping or coating.

4. The apparatus for stimulating the brain and measuring the light induced neuronal activity according to claim 1, wherein the insulation unit is formed to enclose the electrode unit by coating.

5. The apparatus for stimulating the brain and measuring the light induced neuronal activity according to claim 1, wherein the signal application unit comprises a plurality of optic fibers, an end of the signal application unit is tapered, the electrode unit encloses the signal application unit, and the insulation unit encloses part of the electrode unit.

6. The apparatus for stimulating the brain and measuring the light induced neuronal activity according to claim 1, wherein the signal application unit comprises a plurality of signal passages each comprising a signal transmitter which transmits the signal and a clad which encloses the signal transmitter, among the plurality of signal passages, the innermost signal passage has a cylindrical shape, and the remaining plurality of signal passages are laminate around the innermost signal passage, and the effective area of the activation signal may be controlled.

7. The apparatus for stimulating the brain and measuring the light induced neuronal activity according to claim 6, wherein the refractive index of each clad is smaller than the refractive index of the signal transmitter enclosed by the clad.

8. The apparatus for stimulating the brain and measuring the light induced neuronal activity according to claim 6, wherein the effective area of the activation signal is controlled by offsetting the activation signal with the inhibition signal.

9. The apparatus for stimulating the brain and measuring the light induced neuronal activity according to claim 8, wherein the effective area of the activation signal which is transmitted by the signal transmitter is controlled by controlling one or more of the distance between each signal transmitter, the cross section of the signal transmitter which transmits the inhibition signal, and the intensity of the inhibition signal.

10. The apparatus for stimulating the brain and measuring the light induced neuronal activity according to claim 1, wherein the refractive index of each clad is smaller than the refractive index of the signal transmitter enclosed by the clad.

11. The apparatus for stimulating the brain and measuring the light induced neuronal activity according to claim 1, wherein the effective area of the activation signal is controlled by offsetting the activation signal with the inhibition signal.

12. The apparatus for stimulating the brain and measuring the light induced neuronal activity according to claim 11, wherein the effective area of the activation signal which is transmitted by the signal transmitter is controlled by controlling one or more of the distance between each signal transmitter, the cross section of the signal transmitter which transmits the inhibition signal, and the intensity of the inhibition signal.

* * * * *